(12) United States Patent
Bussey et al.

(10) Patent No.: US 9,222,138 B2
(45) Date of Patent: Dec. 29, 2015

(54) THERAPEUTIC TARGETS FOR ADRENOCORTICAL CARCINOMA

(71) Applicants: Kimberly Bussey, Phoenix, AZ (US); Michael J. Demeure, Scottsdale, AZ (US)

(72) Inventors: Kimberly Bussey, Phoenix, AZ (US); Michael J. Demeure, Scottsdale, AZ (US)

(73) Assignees: THE TRANSLATIONAL GENOMICS RESEARCH INSTITUTE, Phoenix, AZ (US); SCOTTSDALE HEALTHCARE CORPORATION, Scottsdale, AZ (US)

( * ) Notice: Subject to any disclaimer, the term of this patent is extended or adjusted under 35 U.S.C. 154(b) by 238 days.

(21) Appl. No.: 13/632,914

(22) Filed: Oct. 1, 2012

(65) Prior Publication Data

US 2013/0122497 A1 May 16, 2013

Related U.S. Application Data

(60) Provisional application No. 61/542,126, filed on Sep. 30, 2011.

(51) Int. Cl.
*C12Q 1/68* (2006.01)
*C12P 19/34* (2006.01)

(52) U.S. Cl.
CPC ........ *C12Q 1/6886* (2013.01); *C12Q 2600/156* (2013.01)

(58) Field of Classification Search
None
See application file for complete search history.

(56) References Cited

PUBLICATIONS

Ou et al; Genome Research, 21:33-46, 2011.*
Dai et al; Pediatrics International; vol. 55; 2013, pp. 368-370.*

* cited by examiner

*Primary Examiner* — Jehanne Sitton

(57) ABSTRACT

This invention identifies and provides a recurrent translocation t(4;8) (p16.2; p23.1) associated with Adrenocortical Carcinoma, and diagnostic methods using the translocation by FISH hybridization or PCR based assays.

5 Claims, 6 Drawing Sheets

SEQUENCE LISTING

```
<160> NUMBER OF SEQ ID NOS: 8

<210> SEQ ID NO 1
<211> LENGTH: 22
<212> TYPE: DNA
<213> ORGANISM: Artificial Sequence
<220> FEATURE:
<223> OTHER INFORMATION: PCR primer for der(4)t(4;8)_4_F

<400> SEQUENCE: 1
ctcgccccac agtatcttat ca                                              22

<210> SEQ ID NO 2
<211> LENGTH: 21
<212> TYPE: DNA
<213> ORGANISM: Artificial Sequence
<220> FEATURE:
<223> OTHER INFORMATION: PCR primer for der(4)t(4;8)_4_R

<400> SEQUENCE: 2
aaaaaccaac ctagggctgt c                                               21

<210> SEQ ID NO 3
<211> LENGTH: 22
<212> TYPE: DNA
<213> ORGANISM: Artificial Sequence
<220> FEATURE:
```

-continued

```
<223> OTHER INFORMATION: PCR primer for der(8)t(4;8)(p16;p23)_Primer_F

<400> SEQUENCE: 3
gatgtgctaa gagtcagctt gc                                              22

<210> SEQ ID NO 4
<211> LENGTH: 21
<212> TYPE: DNA
<213> ORGANISM: Artificial Sequence
<220> FEATURE:
<223> OTHER INFORMATION: PCR primer for der(8)t(4;8)(p16;p23)_Primer_R

<400> SEQUENCE: 4
tgggcaacag tgagactttg t                                               21

<210> SEQ ID NO 5
<211> LENGTH: 35
<212> TYPE: DNA
<213> ORGANISM: Artificial Sequence
<220> FEATURE:
<223> OTHER INFORMATION: synthetic sequence used as PCR primer;
      der(4)t(4;8)_4_2_F

<400> SEQUENCE: 5
gacggccagt acttctttca tctgttttgt gttgg                                35

<210> SEQ ID NO 6
<211> LENGTH: 32
<212> TYPE: DNA
<213> ORGANISM: Artificial Sequence
<220> FEATURE:
<223> OTHER INFORMATION: synthetic sequence used as PCR primer;
      der(4)t(4;8)_4_2_R

<400> SEQUENCE: 6
tatgaccatg agggatggga tctgggtgat ta                                   32

<210> SEQ ID NO 7
<211> LENGTH: 32
<212> TYPE: DNA
<213> ORGANISM: Artificial Sequence
<220> FEATURE:
<223> OTHER INFORMATION: synthetic sequence used as PCR primer;
      der(8)t(4;8)_8_2_F

<400> SEQUENCE: 7
gacggccagt tgacctagcc cctctctttc tc                                   32

<210> SEQ ID NO 8
<211> LENGTH: 31
<212> TYPE: DNA
<213> ORGANISM: Artificial Sequence
<220> FEATURE:
<223> OTHER INFORMATION: synthetic sequence used as PCR primer;
      der(8)t(4;8)_8_2_R

<400> SEQUENCE: 8
tatgaccatg tgacctagcc cctctctttc t                                    31
```

THERAPEUTIC TARGETS FOR ADRENOCORTICAL CARCINOMA

CROSS REFERENCE

This application is related to and claims the priority benefit of U.S. provisional application 61/542,126, filed on Sep. 30, 2011, the teachings and content of which are incorporated by reference herein.

FIELD OF THE INVENTION

This invention relates to a therapeutic target for Adrenocortical Carcinoma (ACC). Further, it relates to methods of using a genomic approach to identify a candidate therapeutic target, and methods of using the target for diagnosis or prognosis testing and drug development.

BACKGROUND OF THE INVENTION

Adrenocortical carcinoma (ACC) is an aggressive malignancy of the adrenal cortex with a poor 5-year survival rate of 10-20%. Many ACC patients have no symptoms until their tumors reach a large size. Currently, there is no reasonably sensitive or specific way to distinguish ACC from the much more common benign adenomas. Right now, diagnosis is made on the basis of tumor size and histopathological features that can be summarized by the Weiss score. Weiss scores of 0 or 1 are considered benign, 2 and 3 are ambiguous, and 4 or larger are cancerous. Histological diagnosis of ACC is difficult to make, which makes treatment decisions complicated. It is evident from gene expression profiling studies that some subset of tumors classified as adenomas turn out to be transcriptionally more similar to ACC. Local recurrence is not sufficient to establish the diagnosis of ACC either. Metastatic disease or invasion into a contiguous structure is the only absolute indicator of malignant disease in masses of the adrenal cortex. In addition to the challenges to the cancer diagnosis, there is a lack of clinical studies to guide therapy. Current therapy is often ineffective and may also be associated with intolerable side effects. Outside of CT or PET scanning, there is no way to evaluate whether treatment is working in reducing tumor burden. Therefore, there is a need to develop a test based on a molecular abnormality in ACC that can be used for identification and quantification of circulating tumor cells at an early stage of the cancer.

SUMMARY OF THE INVENTION

One aspect of the present invention provides a confirmatory diagnostic method for Adrenocortical carcinoma (ACC). The general method comprises the steps of obtaining a sample from a subject suspected to have adrenocortical carcinoma; and detecting a translocation abnormality t(4;8) (p16.2; p23.1) in cells from the sample, wherein the presence of the translocation in more than about 15% of cells scored as positive confirms the diagnosis of ACC.

In some embodiments of the invention, the step of detecting t(4;8) (p16.2; p23.1) in the general method comprises karyotyping interphase chromosomes using fluorescent in situ (FISH) procedures, including multicolor-FISH (mFISH), split-signal FISH (ssFISH), Fusion signal FISH (fs), and any derivative procedure thereof, wherein the procedure comprises one or more probes having sequence complementary to a sequence specific to t(4;8) (p16.2; p23.1). In another embodiment of the invention, the step of detecting t(4;8) (p16.2; p23.1) in the general method comprises analyzing nucleic acid sequences specific to t(4;8) (p16.2; p23.1) using PCR, hybridization, sequencing, or any combination thereof. In yet another embodiment of the invention, the step of detecting t(4;8) (p16.2; p23.1) in the general method comprises analyzing the expression of one or more genes disrupted by t(4;8) (p16.2; p23.1) using PCR, hybridization, sequencing, or any combination thereof.

Another aspect of the invention provides a confirmatory diagnostic method for adrenocortical carcinoma (ACC). The method comprises obtaining a sample from a subject suspected to have adrenocortical carcinoma; and detecting a translocation abnormality t(4;8) (p16.2; p23.1) using karyotyping interphase chromosome by a fluorescent in situ (FISH) procedure wherein the procedure comprises: (i) probes for Chromosome 4 comprising one or more Bacterial Artificial Chromosomes (BACs) selected from the group consisting of: RP11-959C10, CTD2255016 and RP11-803H22; and (ii) probes for Chromosome 8 comprising one or more BACs selected from the group consisting of: RP11-54I15, RP11-1130G3, and CTD-2045B18. In this method, the presence of the translocation in a cell of the sample is signified by a distance between the chromosome 4 probes signal and the chromosome 8 probe signal that is less than a signal's width apart; and the presence of the translocation in more than about 15% of cells scored as having the translocation confirms the diagnosis of ACC.

Additional aspect of this invention comprises a confirmatory diagnostic method for adrenocortical carcinoma (ACC), which comprises obtaining a sample from a subject suspected to have adrenocortical carcinoma; and detecting a translocation abnormality t(4;8) (p16.2; p23.1) using a PCR assay comprising probes that comprise sequences selected from the group consisting of SEQ ID NO. 1, SEQ ID NO. 2, SEQ ID NO. 3, SEQ ID NO. 4, SEQ ID NO. 5, SEQ ID NO.6, SEQ NO. 7 and SEQ NO. 8.

Another aspect of the present invention provides a transgenic animal, comprising t(4;8) (p16.2; p23.1). For example, the transgenic animal may be a mouse.

Yet another aspect of the present invention provides a method for identifying an agent that reduces ACC cell viability. The general method comprises the steps of contacting the cancer cell with an agent, wherein the cancer cell comprises t(4;8) (p16.2; p23.1); and testing one or more cancer cell responses to the agent, wherein the cancer cell response is selected from the group consisting of tumor cell count, metastasis, apoptosis, wherein a lower level of drug target activity, cancer cell count, or metastasis indicates that the agent is a therapeutic agent against ACC; wherein the cancer cell response is compared relative to a control sample. In the general method, the agent is preferably a pharmaceutically active ingredient or pharmaceutically acceptable salt thereof, a drug, a toxin, a chemical, a small organic molecule, a large molecule or peptide, or an antibody.

Other aspects and iterations of the invention are described in more detail below.

DETAILED DESCRIPTION OF THE INVENTION

Figure 1A:
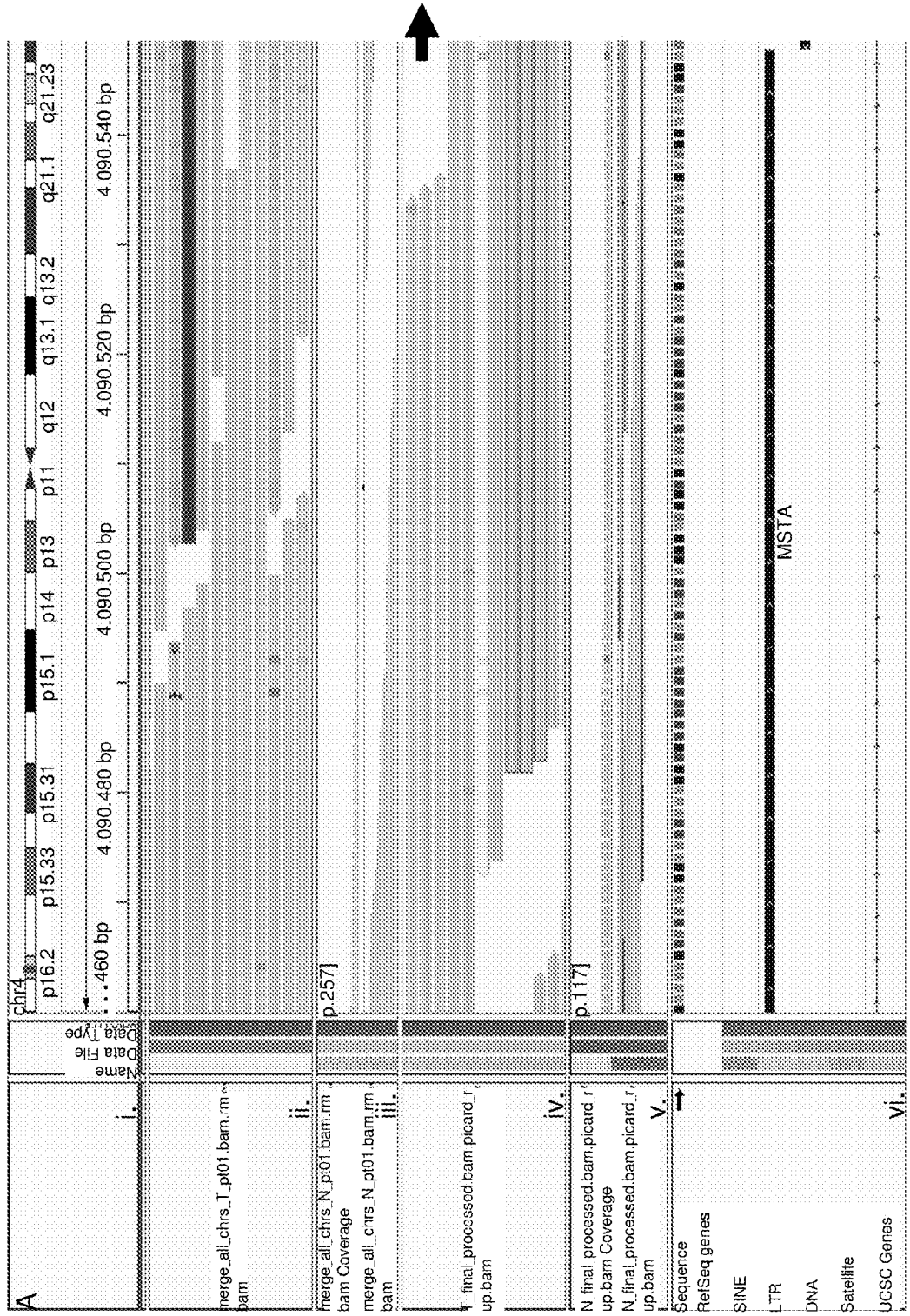
FIG. 1A highlights chromosome 4 and FIG. 1B shows the corresponding jump to chromosome 8.
Figure 1:
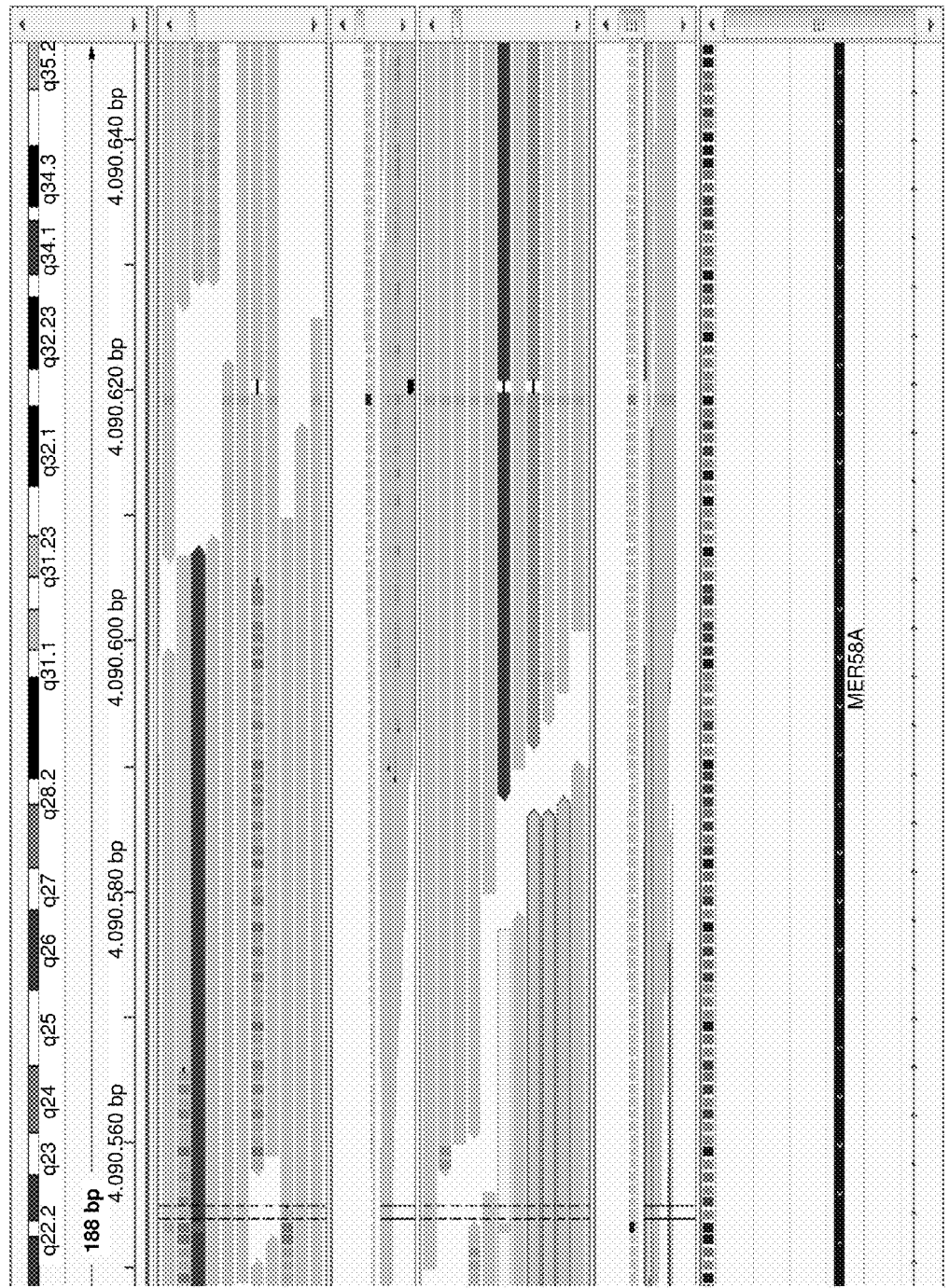
FIG. 1 (divided into FIG. 1A and FIG. 1B) depicts the IGV screen shots of the region of interest from ACC 132.
Figure 1B:
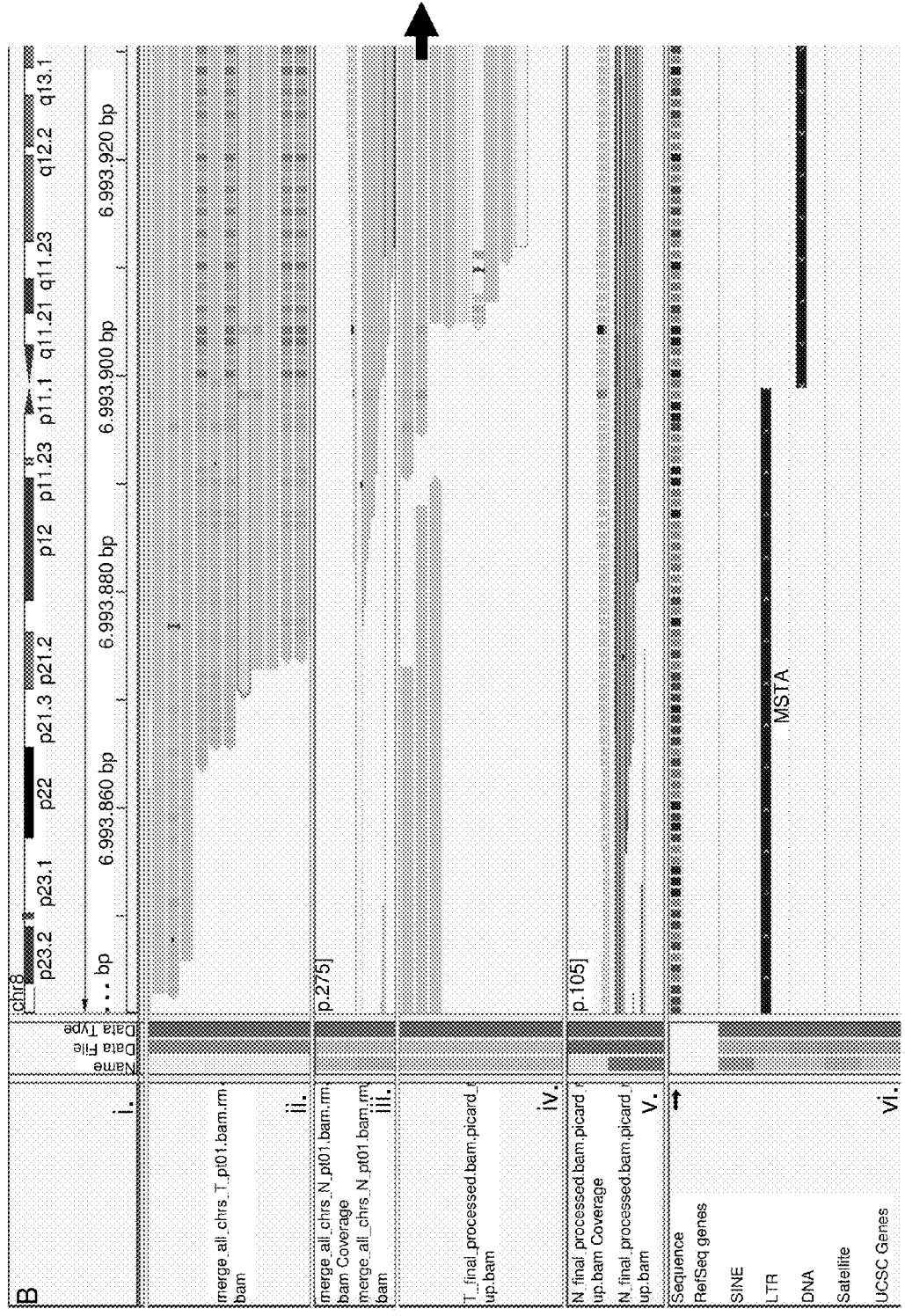
Figure 1:
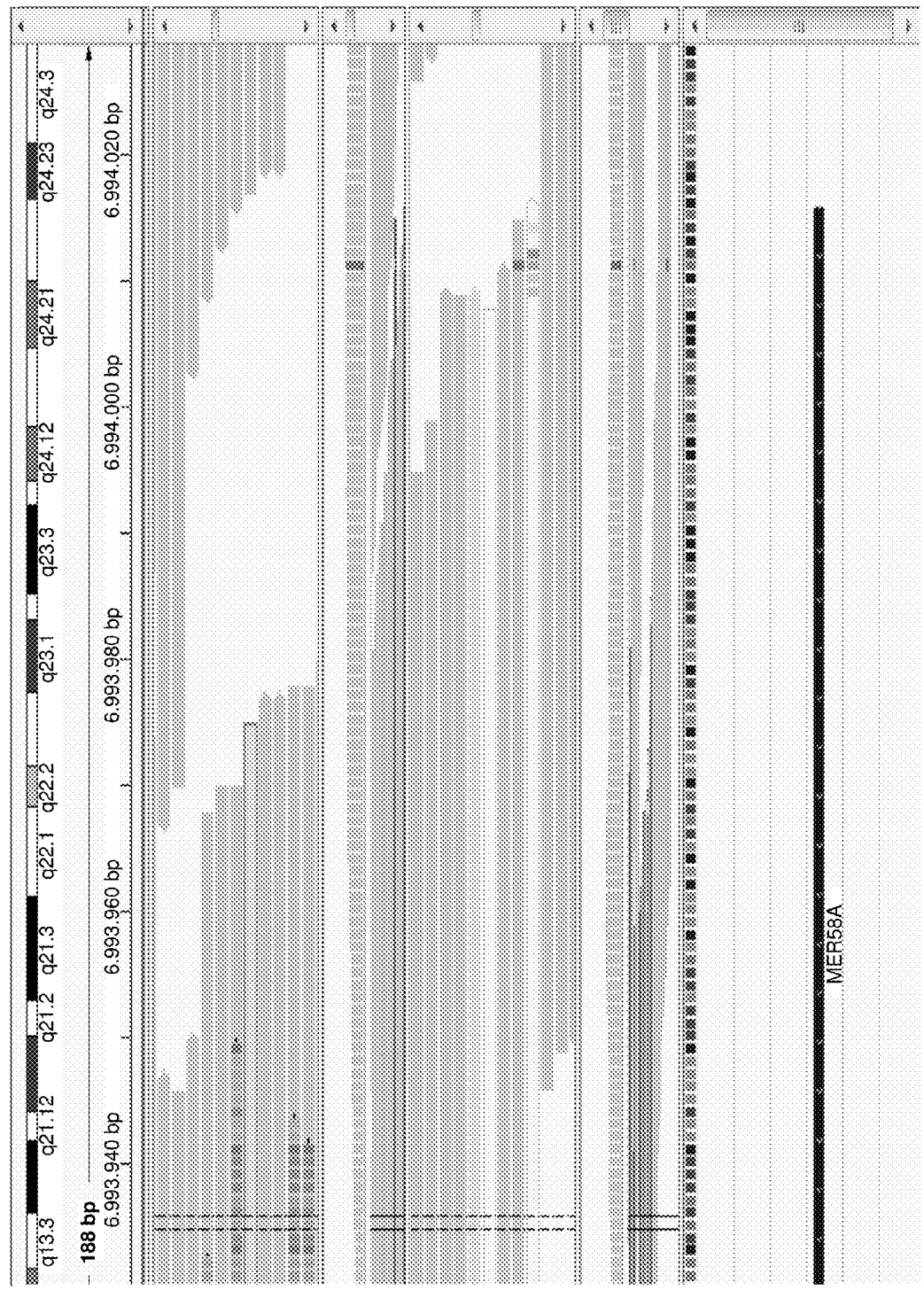

The present invention provides a translocation associated with Adrenocortical Carcinoma (ACC) and a method for ACC diagnosis using the translocation. The invention also provides a transgenic animal comprising the translocation, and a method of identifying ACC therapeutics using the translocation disclosed herein.

Translocations are chromosomal abnormalities which occur when chromosomes break and the fragments of the chromosomes rejoin to other chromosomes. Translocations are often detected on cytogenetics or a karyotype of affected cells. The two principal molecular consequences of translocations are the activation of proto-oncogenes and the creation of novel fusion genes. Translocations are rearrangements between two chromosomes where portions of different chromosomes are exchanged. A translocation is classified as recurrent when it occurs in more than one sample of the same type tumor from different patients.

The present invention provides a recurrent translocation, t(4;8) (p16.2; p23.1), associated with ACC. t(4;8) (p16.2; p23.1) has break points around chr4:4090373—specifically within the short arm of the chromosome 4 region 1 band 6 sub-band 2, and chr8:6993890—specifically within the short arm of the chromosome 8 region 2 band 3 sub-band 1.

Previous work in the field of genomic profiling has used either G-banding or CGH (Comparative genomic hybridization) method. G-banding is a technique used in cytogenetics to produce a visible karyotype by staining condensed chromosomes. G-banding suffers from both a lack of resolution (10 mega base) and ambiguity because banding is not 100% specific for chromosomal regions. Therefore, using G-banding alone would be inadequate for identification of structural rearrangements. CGH involves hybridizing differentially labeled DNA from tumor and a normal control to metaphase chromosomes. The level of resolution obtainable depends on the length of the metaphase chromosomes and has a limit of 10 Mb as well. Therefore, CGH cannot detect structural rearrangements like translocations. Further, the prevalent genomic duplication, although likely facilitating DNA rearrangement, prevents absolute determination of the rearrangement by analysis of the sequence alone. Thus, neither of these techniques can be readily used to detect the discovered abnormality. In one embodiment of the invention, the combination of spectral karyotyping and DNA sequencing of the entire genome of the ACC cell lines, allowing for a more precise identification of structural rearrangements, was used to detect the recurrent translocation t(4;8) (p16.2; p23.1). The ACC cell lines that may be used for spectral karyotyping are selected from a group consisting of SW-13, H295, H295R, and any derivatives thereof. In one embodiment, the ACC cell lines used for spectral karyotyping are SW-13 and H295R. The DNA sequencing is preferably in-depth, whole genome sequencing in the regions implicated by cell line spectral karyotyping in one or more ACC tumors.

In another aspect of the present invention, a recurrent translocation associated with ACC tumors can be used to develop a diagnostic test for ACC. The presence of a target recurrent translocation may be detected by methods that are PCR-based, hybridization-based, sequencing-based, or any combination of the above methods or derivatives thereof. The detection may be through various methods including, but not limited to, PCR-based methods including real-time PCR, quantitative PCR, and quantitative real time PCR.

In one embodiment, the diagnostic test is a FISH-based molecular cytogenetics assay. The technique generally entails preparing a sample, labeling probes, denaturing target chromosomes and the probe, hybridizing the probe to the target sequence, and detecting a signal.

In one embodiment, the test is a multicolor-FISH technique (m-FISH or multiplex FISH) such that each separate normal chromosome is stained by a separate color. In another embodiment, split-signal FISH (ssFISH) detects changes in chromosomal structure by using two probes, each of which is labeled by a different detectable label. Preferably, the detectable labels should be distinguishable from one another. Each probe binds to the chromosome on either side of a suspected breakpoint in the chromosome. In a normal chromosome, the two probes will be proximal enough to each other such that the combined signal of their different labels forms a signal that is different from each label alone. Thus, a normal chromosomal sample will contain only the combined or fused signal of the two probes on the sister chromosomes. In an abnormal sample, where one sister chromosome has broken at the suspected break point, the fused signal will remain on the normal sister chromosome. On the broken chromosome, one probe migrates to a different chromosome, where the individual signal of that probe becomes apparent. The other individual probe remains on the split chromosome and, because it is no longer proximal to the other probe, emits its individual signal as well. In sum, because of the break in chromosomal structure, the two probes are no longer juxtaposed, allowing the fused signal they form together to split into the individual signals for each probe.

Fusion-signal FISH is similar to ssFISH in that two probes with two different, distinguishable labels are used such that proximity of the two labels produces a new fused signal. The two methods differ in that for fusion-signal FISH, the two probes bind to two different chromosomal pairs at locations that are suspected to become proximal to each other as a result of a chromosomal rearrangement. Thus, in a normal sample, only signals from the individual probes are present and no fused signal appears. In an abnormal sample, where a piece of one chromosome has attached to another chromosome, the normal chromosomes in each of the two pairs involved will still emit each of the individual probe signals. In the abnormal chromosome, in which the probes are now proximal due to the translocation, the fused signal appears.

Alternatively, a diagnostic test in another embodiment is a PCR-based method detecting the presence of the translocation. In addition, the recurrent translocation t(4;8) (p16.2; p23.1) involves two genes of unknown function (BC042823 (uc003gho.2, IMAGE:5275587) on chromosome 4 and BC030294 (IMAGE:5396854) on chromosome 8 to create a fusion gene. Translocation may result in a disrupted gene or a gene fusion. Therefore PCR-based methods can be used to detect those events as well. The disruption of a gene may lead to an increased or decreased expression level, and/or altered expression specificity. As used herein, a gene fusion refers to an accidental joining of the DNA of two genes. Gene fusions may give rise to hybrid proteins or the misregulation of the transcription of one gene due to the juxtaposition of cis regulatory elements (e.g., enhancers or promoters) of another gene. In one embodiment of the diagnostic test based on t(4;8) (p16.2; p23.1), the test is to detect the expression level of one or both of the genes if the gene is disrupted due to the translocation. In another embodiment, the test is to detect the presence of a hybrid nucleic acid or protein.

In calculating the expression of a target gene in relation to an adequate reference gene, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithms.

The algorithm for Ct values in RT-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of the respective target that the primer sets are designed to recognize. If the target is missing in a sample, there should be no amplification in the RT-PCR reaction. Alternatively, the Cp value may be utilized. Cp value represents the point in the cycle at which the increase of fluorescence is highest and where the logarithmic phase of a PCR reaction begins. For example, the LightCycler® 480 Software (Roche Applied Science, Penzberg, Germany) calculates the second derivatives of entire amplification curves and determines where this value is at its maximum. By using the second-derivative algorithm, data obtained are more reliable and reproducible, even if fluorescence is relatively low. The expression of the biomarker or target in the test subject may be 1,000,000×, 100,000×, 10,000×, 1000×, 100×, 10×, 5×, 2×, 1×, 0.5×, 0.1×, 0.01×, 0.001×, 0.0001×, 0.00001×, 0.000001×, or 0.0000001× of the predetermined level indicating the presence or absence of a cellular or physiological characteristic. The predetermined level of expression may be derived from a single control sample or a set of control samples.

The various and non-limiting embodiments as described herein may comprise one or more probes and/or primers. Generally, the probe or primer contains a sequence complementary to a sequence specific to the region of the translocation, or specifically to the genes in the region of translocation. A homologous sequence having less than 60% 70%, 80%, 90%, 95%, 99% or 100% identity to the identified gene sequence may also be used for probe or primer design if it is capable of binding to its complementary sequence of the desired target sequence in the region of translocation under stringent condition. "Homologous" refers to any probe which can hybridize to either or both strands of the double-stranded nucleic acid sequence under conditions ranging from low to high levels of stringency.

Low stringency conditions, when used in reference to nucleic acid hybridization, comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pfizer, New York, N.Y.), 5 g BSA (Fraction V; Sigma-Aldrich, St. Louis, Mo.)] and 100 μg/ml denatured salmon sperm DNA followed by washing in a solution comprising 5×SSPE, 0.1% SDS at 42° C. when a probe of about 500 nucleotides in length is employed.

High stringency conditions, when used in reference to nucleic acid hybridization, comprise conditions equivalent to binding or hybridization at 42° C. in a solution consisting of 5×SSPE (43.8 g/l NaCl, 6.9 g/l $NaH_2PO_4 \cdot H_2O$ and 1.85 g/l EDTA, pH adjusted to 7.4 with NaOH), 0.5% SDS, 5×Denhardt's reagent and 100 μg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

Generally, nucleic acid based probes and primers are complementary to a sequence within the target DNA sequence region. Probes may include one or more labels. A label may be any substance capable of aiding a machine, detector, sensor, device, or enhanced or unenhanced human eye from differentiating a labeled composition from an unlabeled composition. Examples of labels include, but are not limited to: a radioactive isotope or chelate thereof, dyes (fluorescent or nonfluorescent,) stains, enzymes, or nonradioactive metals. Specific examples include, but are not limited to: fluorescein, biotin, digoxigenin, alkaline phosphatese, biotin, streptavidin, $_3H$, $_{14}C$, $_{32}P$, $_{35}S$, or any other compound capable of emitting radiation, rhodamine, 4-(4_-dimethylaminophenylazo) benzoic acid ("Dabcyl"), 4-(4_-dimethylamino-phenylazo)sulfonic acid (sulfonyl chloride) ("Dabsyl"), 5-((2-aminoethyl)-amino)-naphtalene-1-sulfonic acid ("EDANS"), psoralene derivatives, haptens, cyanines, acridines, fluorescent rhodol derivatives, cholesterol derivatives, ethylenediaminetetraaceticacid ("EDTA") and derivatives thereof, or any other compound that may be differentially detected. The label may also include one or more fluorescent dyes optimized for use in genotyping. Examples of such dyes include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, Cy3, Cy5, LIZ, and Texas Red.

The detection of fusion protein due to the translocation may be through novel epitopes recognized by polyclonal and/or monoclonal antibodies used in ELISA, immunoblotting, flow cytometric, immunohistochemical, and other mutant protein detection strategies (as described in Wong et al., Cancer Res., 46: 6029-6033, 1986; Luwor et al., Cancer Res., 61: 5355-5361, 2001; Mishima et al., Cancer Res., 61: 5349-5354, 2001; Ijaz et al., J. Med. Virol., 63: 210-216, 2001, the teachings and content of which are incorporated by reference herein). The term "antibody" is used herein in the broadest sense and refers generally to a molecule that contains at least one antigen binding site that immunospecifically binds to a particular antigen target of interest. The term antibody thus includes, but is not limited to, native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. The term thus includes full length antibodies and/or their variants as well as immunologically active fragments thereof, thus encompassing antibody fragments capable of binding to a biological molecule (such as an antigen or receptor) or portions thereof, including but not limited to Fab, Fab', F(ab')2, facb, pFc', Fd, Fv or scFv (See, e.g., CURRENT PROTOCOLS IN IMMUNOLOGY, (Colligan et al., eds., John Wiley & Sons, Inc., NY, 1994-2001)).

The sample in this general diagnostic method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus, and the like; an extract from a cell, chromosome, organelle, or membrane isolated from a cell; a cell; genomic DNA, RNA, or cDNA, in solution or bound to a substrate; a tissue; a tissue print; or any other material isolated in whole or in part from a living subject. Such samples include, but are not limited to, tissue isolated from primates, e.g., humans, or rodents, e.g., mice, and rats. Biological samples may also include sections of tissues such as biopsy and autopsy samples, and frozen sections taken for histologic purposes such as blood, plasma, serum, sputum, stool, tears, mucus, hair, skin, and the like. Biological samples also include explants and primary and/or transformed cell cultures derived from patient tissues. The term "subject" is used in its broadest sense. In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer.

The probes and primer sequences to work with PCR, for example, include: der(4)t(4;8)_4_F: ctcgccccacagtatcttatca (SEQ ID NO. 1); der(4)t(4;8)_4_R: aaaaaCCAAC-CTAGGGCTGTC (SEQ ID NO. 2); der(8)t(4;8)(p16;p23)_Primer_F: gatgtgctaagagtcagcttgc (SEQ ID NO. 3) and der(8)t(4;8)(p16;p23)_Primer_R: tgggcaacagtgagactttgt (SEQ ID NO. 4); der(4)t(4;8)_4_2_F: GACGGCCAGTACT-TCTTTCATCTGTTTTGTGTTGG (SEQ ID NO. 5); der(4)t(4;8)_4_2_R: TATGACCATGAGGGATGG-GATCTGGGTGATTA (SEQ ID NO. 6); der(8)t(4;8)_8_2_F: GACGGCCAGTTGACCTAGCCCCTCTCTTTCTC (SEQ ID NO. 7) and der(8)t(4;8)_8_2_R: TATGACCAT-GTGACCTAGCCCCTCTCTTTCT (SEQ ID NO. 8). FISH probes for Chromosome 4 are BACs (Bacterial Artificial Chromosome): RP11-959C10, CTD2255016, RP11-803H22, RP11-351L3, RP11-357G3, and RP11-687G23. FISH probes for Chromosome 8 are BACs: RP11-54I15, RP11-1130G3, RP11-826L17, RP11-623J22 and CTD-2045B18.

The various embodiments of the test developed based on the ACC associated recurrent translocation t(4;8) (p16.2; p23.1) may be used to monitor disease progression or as a companion test for ACC therapeutics.

There are only a few widely available ACC cell lines, including SW13, H295 and H295R. ACC is rare in mice. Another aspect of the invention provides a cell line cell or a genetically modified animal comprising the ACC associated recurrent translocation t(4;8) (p16.2; p23.1). In another embodiment, the cell line cell or the genetically modified animal comprises the disrupted gene or gene fusion in the region of the recurrent translocation t(4;8) (p16.2; p23.1). For example, such a transgenic mouse model may then serve as an animal model to evaluate new therapies for the treatment of patients with ACC.

The development of novel pharmaceutical therapeutics relies on the identification and validation of key regulators of a drug targets, which may be the disrupted, or the fusion gene involved in the region of the ACC associated recurrent translocation t(4;8) (p16.2; p23.1).

Another aspect of the invention provides methods for identifying an ACC therapeutic agent through a drug target based on the recurrent translocation as disclosed herein. The methods comprise contacting a test agent with a cell comprising a therapeutic target that is expressed in the cell. An agent that is an inhibitor of cancer condition may be identified by determining the effect of a test agent on the expression level of a target. In a particular example, a test agent that down-regulates the target expression as compared to the target expression in the absence of the test agent identifies that test agent as an inhibitor of a target.

Inhibitors of drug target gene or protein expression may be any agent including a pharmaceutically active ingredient or pharmaceutically acceptable salt thereof, a drug, a toxin, a chemical, a small organic molecule, a large molecule or peptide, or an antibody. Large-molecule pharmaceuticals refer to pharmaceutical agents having a molecular weight greater than about 1000 daltons, e.g. peptidic drugs, vaccines and hormones. The term "antibody" has the same definition as provided herein.

The screening or creation, identification, and selection of appropriate inhibitors of drug targets for ACC can be accomplished by a variety of methods. One approach is to use structural knowledge about the target protein to design a candidate molecule with which it will precisely interact. An example would be computer assisted molecular design. A second approach is to use combinatorial or other libraries of molecules, whereby a large library of molecules is screened for inhibitory effect with regard to the target gene or protein expression, or ability to inhibit the transcriptional factor activity of the target protein. In a further example, a panel of antibodies may be screened for ability to inhibit the target protein.

Cancer and precancer may be thought of as diseases that involve unregulated cell growth. Metastasis involves migration of tumor cells away from the site of the primary tumor, entry into the circulation, and proliferation at a new site. Cell growth involves a number of different factors. One factor is how rapidly cells proliferate, and another involves how rapidly cells die. Cells can die either by necrosis or apoptosis depending on the type of environmental stimuli. Cell motility is yet another factor that influences tumor growth kinetics and metastasis. Resolving which of the many aspects of cell growth a test agent affects can be important to the discovery of a relevant pharmaceutical therapy for ACC cancer cells. Screening assays based on this technology can be combined with other tests to determine which agents have growth inhibiting and pro-apoptotic activity in ACC cancer cells.

Some embodiments provided herein involve determining the ability of a given agent to inhibit the expression of the ACC drug targets. Test agents can be assessed for their probable ability to inhibit growth or otherwise alter the behavior of ACC cancer cells. Various cell lines can be used and could be selected based on the tissue to be tested. Certain cell lines are well characterized, and are used, for instance, by the United States National Cancer Institute (NCl) in their screening program for new anti-cancer drugs. Cell lines can also be constructed to overexpress the ACC drug targets for screening inhibitory agents for ACC cancer cells. Significant tumor cell growth inhibition, greater than about 30% at a dose of 100 1.1M or below, is further indicative that the agent is useful for treating the ACC. An $IC_{50}$ value may be determined and used for comparative purposes. This value is the concentration of drug needed to inhibit tumor cell growth by 50% relative to the control. In some embodiments, the $IC_{50}$ value is less than 100 μM in order for the agent to be considered further for potential use for treating, ameliorating, or preventing tumor metastasis.

EXAMPLES

The following non-limiting examples are included to illustrate the invention, and they are not intended to limit the scope of the claims.

Example 1

Whole Genome Sequencing on an ACC Tumor and Matched Peripheral Blood

Clinical Synopsis: A 51 year old female presented with abdominal fullness and pressure after eating. A CT scan demonstrated a 9.5 cm left adrenal tumor. She had no excess adrenal hormone on functional testing. She underwent a laparoscopic left adrenalectomy with tumor capsule fracture. Three years later, she was found to have local recurrence by CT and was started on mitotane for about 6 months during which time the tumors continued to grow. She was then referred for the OSI-906 trial study, on which she remained for 8 months. There was no evidence of distant disease, so the patient was returned to the operating room for resection of the locally recurring intraperitoneal disease 4 years after presentation. Multiple areas of recurrent ACC were resected from the omentum, along the left kidney, aorta, descending colon and the diaphragm. The largest focus of cancer was 14.5 cm. The modified Weiss score of this sample was 4. After this operation, she received adjuvant chemotherapy in the form of 4 cycles of etoposide, cisplatin and doxorubicin. Six months after surgery, her CT showed no evidence of recurrence.

Sequencing: DNA extracted from both tumor and blood was processed independently, and libraries were paired-end sequenced on the Illumina HiSeq 2000 platform (Illumina, Inc., San Diego, Calif.).

Analysis: Sequencing data was aligned to the reference genome, build hg18. Variations were predicted in the tumor and blood separately using two different SNP calling algorithms: Varscan (Washington University, St. Louis, Mo.) and an internal caller (TGen, Phoenix, Ariz.). After SNP prediction, results were combined to identify variations called by both algorithms, submitted to PolyPhen2 to assess predicted functional consequence, and filtered to yield those SNPs most likely to represent deleterious, non-synonymous changes in coding regions of the genome in the tumor specifically, as well as those shared by the tumor and blood (i.e., constitutional changes). Copy number variation was computed. Further analysis of structural variation included indels and translocations. ACC is not characterized by mutations in commonly altered cancer genes, and the same observation was obtained from the two ACC cell lines, SW-13 and H295, as well.

Example 2

The Translocation Discovered Using a Genomic Approach

The combination of spectral karyotyping and DNA sequencing of the entire genome of the ACC cell lines allows more precise identification of structural rearrangements. The translocation was discovered by analyzing the data from the first in-depth, whole genome sequencing of two ACC tumors in regions implicated by the spectral karyotyping of the two ACC cell lines, SW-13 and H295R. A recurrent translocation, t(4;8)(p16.2;p23.1) with break points around chr4:4090373 and chr8:6993890.

Example 3

The Translocation Validation

Figure 2:
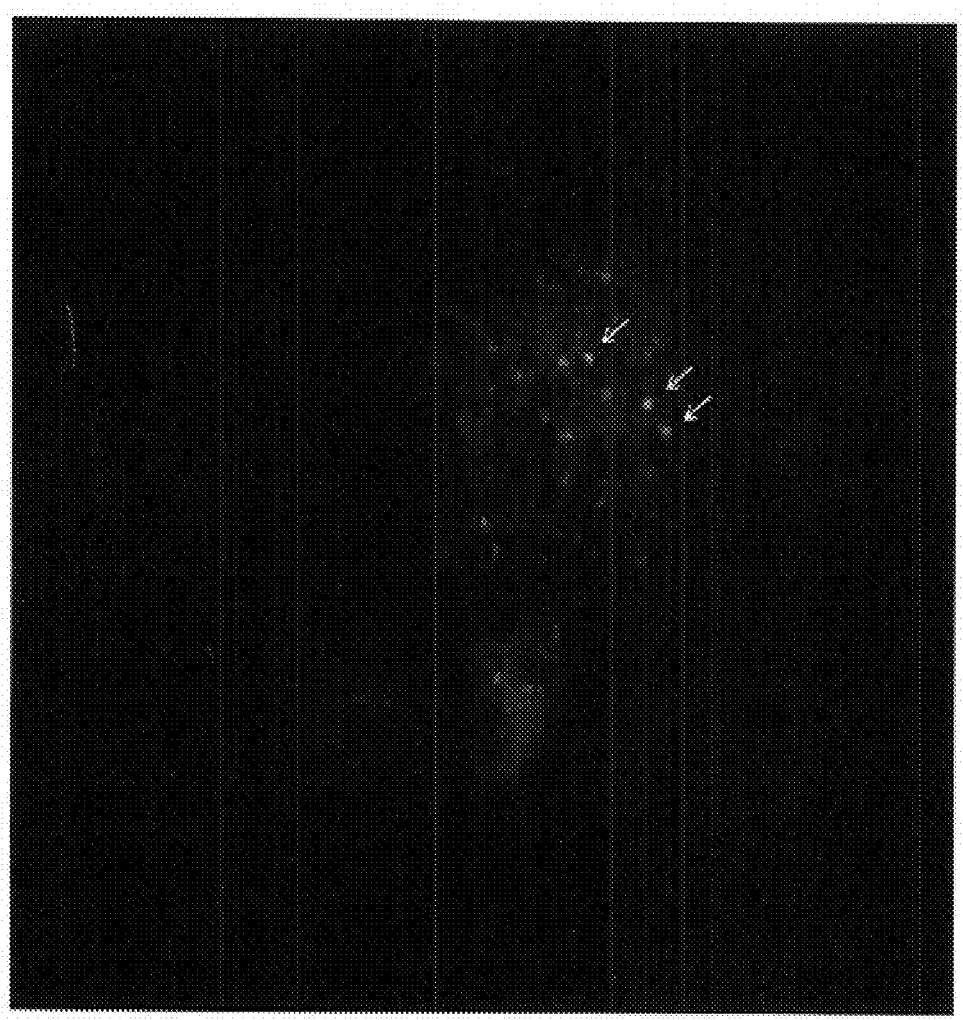
FIG. 2 depicts the fluorescent in situ hybridization (FISH) with RP11-959C10 (red) and RP11-54I15 (green). There is evidence for co-localization with yellow signals (arrows)

The translocation was validated by fluorescent in situ (FISH) in an ACC cell line from a different tumor using BACs spanning the putative breakpoints. Two BACs spanning the break points: Chr 4: RP11-959C10 (TAMRA labeled, red) Chr 8: RP11-54115 (FITC labeled, green) were discovered. The two BACs were labeled fluorescently and used to FISH in ACC 140-1, a cell line derived from another ACC tumor. Theoretically, the red and green probes would hybridize to the breakpoint and appear to co-localize, identifying the existence of the translocation, and thus give a yellow signal. In comparison, normal chromosomes 4 and 8 without translocation would have green or red signals, respectively. As shown in FIG. 2, there was evidence of co-localization.

Figure 3:
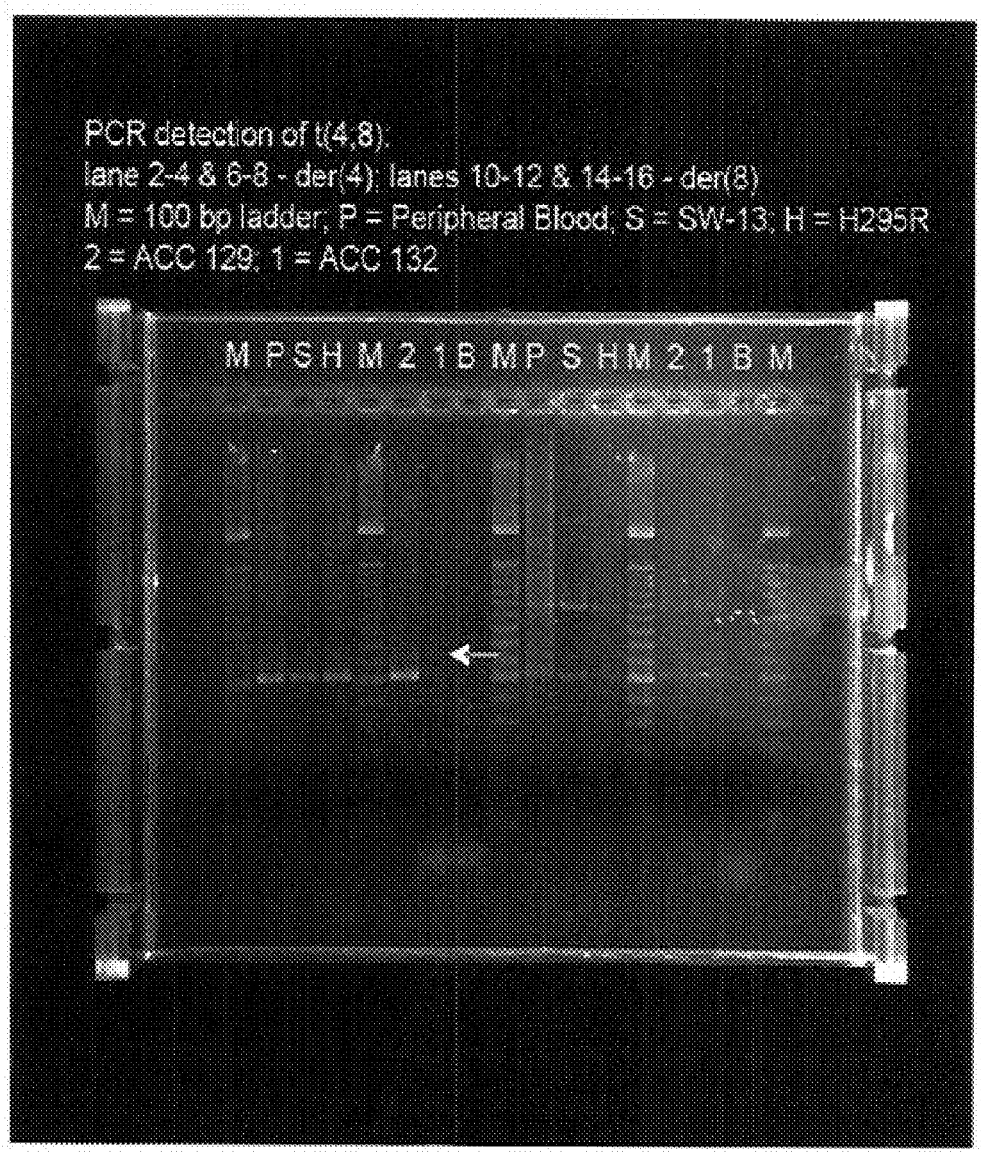
FIG. 3 depicts the PCR amplification of putative translocation breakpoints. The der(4) product is in lanes 2-4 and 6-8, and the der(8) product is in lanes 10-12 and 14-16. The ladder is a 100 bp ladder. Amplification of ~700 bp fragment was seen in the der(4)t(4;8)(p16.2;p23.1) PCR. The predicted 517 bp product of the der(8)t(4;8)(p16.2;o23.1) was not observed.

The presence of the translocation was also validated using PCR to amplify the putative breakpoints. The putative translocation products have distinct sizes from the other PCR products and can be resolved by gel electrophoresis. FIG. 3 shows the presence of a ~700 bp fragment in H295R.

Example 4

Prevalence and Specificity of the Translocation in ACC

The recurrent translocation, t(4;8)(p16.2;p23.1), with break points around chr4:4090373 and chr8:6993890, was shown to lie near to one another in normal cells. This information was utilized in setting a scoring criteria for the FISH protocol in detecting this t(4;8) translocation in both metaphase spreads and interphase nuclei. In the FISH protocol, an interphase cell was scored as positive if the distance between the chromosome 4 probe signal and the chromosome 8 probe signal is less than a signal's width apart. Interphase FISH to normal blood were carried out to evaluate t(4;8) translocation in both interphase cells and metaphase spreads as control, which demonstrated a background rate of 10 false positives for every 100 interphase cells scored. There were no metaphase spreads found positive for the t(4;8) translocation in normal blood. However, in the evaluation of metaphase spreads in the cells from ACCs that carry the translocation, a portion of the metaphase spreads were found to be positive for the t(4;8) translocation. The data suggested that samples having more than about 15% of cells scored as positive in t(4;8) translocation can be reliably called positive. Table 1 lists the ranges of positive scores from the tumor samples comprising nuclei from fresh frozen tissues.

TABLE 1

T(4; 8) Scoring in Tumor Samples

| | Sample Type | | | |
|---|---|---|---|---|
| | ACC tumor | Adrenal Adenoma | Non-ACC Malignant Tumor | Non-ACC Benign Tumors |
| Number of Tumors Assayed | 5 | 2 | 3 | 2 |
| Range of positive cells/100 cells scored | 18-30 | 11-17 | 25-31 | 15-16 |

Table 1 demonstrates that 1) ACC tumor samples usually have 20-30% positive cells and 2) other malignant tumors are also scoring as positive in the range of 20-30% cells. This suggests that although the translocation is not ACC specific, it is specific for malignant tumors, much like mutations in p53 are not specific for a particular type of cancer but can be found in 50% of all malignant tumors.

Various cell lines were also scored for the recurrent translocation, t(4;8)(p16.2;p23.1). Those cell lines included: HCT116 (Human Colorectal Carcinoma cell line); ACC167 (Human Adrenocortical Carcinoma); H295R cell line (Human Adrenocortical Carcinoma); SW-13 (Human Adrenocortical Carcinoma); ACC140-1 (Human Adrenocortical Carcinoma). Table 2 lists the ranges of positive scores from these cell lines.

TABLE 2

T(4; 8) Scoring in Cell lines

| Cell Type | HCT116 | ACC167 | H295R | SW-13 | ACC140-1 |
|---|---|---|---|---|---|
| Range of positive cells/100 cells scored | 2/100 | 11/100 | 10/100 | 31/100 | 18/100 |

Example 5 t(4;8) Translocation as a Therapeutic Target of ACC

Tumor samples, both benign and malignant as well as ACC and non-ACC were assayed to determine exactly what the prevalence is for different diagnoses. In addition, the t(4;8) translocation was not found in all ACC cells, and thus, it is a necessary but not sufficient event in the development of ACC. The fact that t(4;8) translocation is maintained in the tumor and not lost completely suggests that this translocation represents a novel therapeutic target. The RNA-sequencing data of three ACC tumors provided such evidence that altered transcription from this region were discovered. PCR assay was designed to detect the predicted products and to show consistent transcription alteration from all three tumors. Part of the products showed homology to LOC100506990, which is predicted to be uncharacterized LOC100506990 gene (GeneBank Access No: NR_040091.1).

Example 6

Prevalence and Specificity of the Translocation in ACC

An interphase FISH screening with the probe sets comprising Chromosome 4 probe (RP11-959C10, CTD2255016, RP11-803H22, RP11-351L3, RP11-357G3, or RP11-687G23) and Chromosome 8 probe (RP11-54I15, RP11-1130G3, RP11-826L17, RP11-623J22 or CTD-2045B18) combinations thereof may be used to screen tumors, both benign and malignant, in an in-house adrenal tumor repository (TGen, Phoenix, Ariz.). Both fusion and split-apart FISH designs are possible with these probes. Probes were labeled either red or green, and hybridized either to nuclei dissociated from frozen tissue or to FFPE tissues. 100-300 nuclei were then scored for either co-localization (in the case of a fusion design) or dissociation (in case of a split-apart design) and compared to the pattern observed on normal tissue.

Example 7

Functional Characterization of the Product of the Translocation siRNA may be designed to target the two genes involved in the translocation. The translocation product selected will be a knockdown or knock-out using the siRNA. The capability of adrenocortical cell transforming and the condition for transformation is then determined. The phenotypes of the ACC cells such as apoptosis, autophagy, decreased proliferation, decreased migration, inhibition of cell signaling pathways, etc. may be analyzed to facilitate ACC therapeutic development.

The invention claimed is:

1. A confirmatory diagnostic method for Adrenocortical carcinoma (ACC), comprising
    obtaining a tissue sample from a human subject suspected to have adrenocortical carcinoma; and
    detecting a translocation abnormality t(4;8) (p16.2; p23.1) in cells from the tissue sample by karyotyping inter phase chromosomes using a fluorescent in situ (FISH) procedure comprising:
    hybridizing one or more probes for Chromosome 4 comprising a Bacterial Artificial Chromosome (BAC) selected from the group consisting of: RP11-959C10, CTD2255016, RP11-803H22, RP11-351L3, RP11-357G3, and RP11-687G23; and hybridizing one or more probes for Chromosome 8 comprising a BAC selected from the croup consisting of: RP11-54I15, RP11-1130G3, RP11-826L17, RP11-623J22 and CTD-2045B18;

wherein the probe for Chromosome 4 and the probe for Chromosome 8 are labeled differently and the presence of a translocation in a cell of the sample is signified when the distance between the signal from a chromosome 4 probe and the signal from a chromosome 8 probe is less than a signal's width apart; and wherein the presence of the translocation in more than 15% of cells scored as positive confirms the diagnosis of ACC.

2. The method of claim 1, wherein the FISH procedure is selected from the group consisting of multicolor-FISH (mFISH), split-signal FISH (ssFISH), and Fusion signal FISH (fs).

3. The method of claim 1, wherein the tissue sample is a tumor sample.

4. The method of claim 1, wherein the tissue sample is from an adrenal gland.

5. The method of claim 1, wherein the human subject suspected to have adrenocortical carcinoma has a family history of cancer.

\* \* \* \* \*